(12) United States Patent
Zlicar et al.

(10) Patent No.: US 6,509,479 B1
(45) Date of Patent: Jan. 21, 2003

(54) PROCESS FOR THE REMOVAL OF A SILYLOXY PROTECTING GROUP FROM 4-SILYLOXY-TETRAHYDRO-PYRAN-2-ONES

(75) Inventors: Marko Zlicar, Celje (SI); Rudolf Rucman, Ljubljana-Smartno (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/869,372

(22) PCT Filed: Feb. 2, 2000

(86) PCT No.: PCT/IB00/00105
§ 371 (c)(1),
(2), (4) Date: Sep. 21, 2001

(87) PCT Pub. No.: WO00/46217
PCT Pub. Date: Aug. 10, 2000

(30) Foreign Application Priority Data

Feb. 4, 1999 (SI) .................................................. 9900025

(51) Int. Cl.⁷ ............................................ C07D 309/30
(52) U.S. Cl. ...................................................... 549/292
(58) Field of Search ......................................... 549/292

(56) References Cited

U.S. PATENT DOCUMENTS

| 4,444,784 A |   | 4/1984 | Hoffman et al. ............. 424/279 |
| 5,021,453 A | * | 6/1991 | Joshua et al. ................ 514/510 |
| 5,041,562 A | * | 8/1991 | Stokker et al. .............. 549/292 |

FOREIGN PATENT DOCUMENTS

EP        0 349 063 A2    1/1990

* cited by examiner

*Primary Examiner*—Alan L. Rotman
*Assistant Examiner*—Raymond Covington
(74) *Attorney, Agent, or Firm*—Bromberg & Sunstein LLP

(57) ABSTRACT

This invention relates to a novel method for the removal of a silyl protecting group from the 4-hydroxy group of tetrahydropyran-2-ones, which method is particularly suitable in the process for the preparation of simvastatin and derivatives and analogs thereof.

13 Claims, No Drawings

PROCESS FOR THE REMOVAL OF A SILYLOXY PROTECTING GROUP FROM 4-SILYLOXY-TETRAHYDRO-PYRAN-2-ONES

This application is a 371 of PCT/IB00/00105 filed Feb. 2, 2000.

FIELD OF THE INVENTION

This invention relates to a novel method for the removal of a slilyl protecting group from the 4-hydroxy group of tetrahydropyran-2-ones, which method is particularly suitable in the process for the preparation of simvastatin and derivatives and analogs thereof.

BACKGROUND OF THE INVENTION

Lovastatin, pravastatin, simvastatin, mevastatin, atorvastatin, fluvastatin, cervastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, and some are obtained by treating the fermentation products using the methods of chemical synthesis (simvastatin) or they are the products of total chemical synthesis (atorvastatin, fluvastatin).

Processes for the preparation of simvastatin and derivatives and analogs thereof generally involve silyl group protection of the 4-hydroxy group which must be eventually removed, typically in the last step of the synthetic route. In the literature processes for the deprotection (desylation) are disclosed using either tetra-n-butylammonium fluoride in acetic acid (U.S. Pat. No. 4,444,7184) or in acetic/trifluoroacetic acid (EP 0 349 063), or with hydrogen fluoride in pyridine (EP 0 349 063), or in acetonitrile (EP 0 331 240). In one of more recent processes (EP 0 444 888) the deprotection has been accomplished with boron trifluoride etherate. The deprotection may also be accomplished using methanesulfonic acid that causes opening of the lactone ring which necessitates the introduction of a lactonization step into the synthesis step.

Use of hydrogen fluoride on a large scale should be avoided due to its strong corrosive and toxic properties. Tetra-n-butylammonium fluoride is less corrosive and toxic, however, it is very expensive and its use strongly increases the cost of the process for the preparation of the final product. Additionally, it imposes a problem in regeneration of the solvents since the fluoride ions remain both in the aqueous and organic phases which is undesirable in view of the ecology and the economy of the process itself. Boron trifluoride etherate is a highly inflammable fluid which diminishes its usable value in the industrial process. Apart from the aforementioned, a number of colored by-products formed during the deprotection reaction result from using the above procedures. Since it is the final step in the synthesis and the final product should be of pharmaceutically acceptable purity, it is desirable the final product of the synthesis is as pure as possible thereby avoiding the introduction of additional isolation steps, such as recrystallization, chromatography or extraction. In the process of purification of the desired final product side products, which by their chemical and physical properties are very similar to the final product, also impose a problem and it is very difficult to separate them from the final product in the industrially acceptable procedure.

DESCRIPTION OF THE INVENTION

In order to solve the above problems of the prior art, the present invention provides a novel deprotection method for the preparation of a compound of the following formula (I)

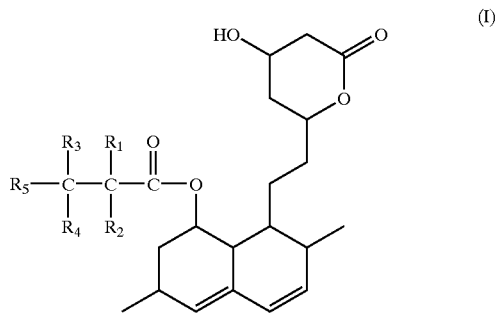

wherein
- $R_1$ and $R_2$ are independently hydrogen or alkyl with one to ten C atoms;
- $R_3$ and $R_4$ are independently hydrogen or alkyl with one to three C atoms;
- $R_5$ is hydrogen, halogen or alkyl with one to three C atoms;

wherein the method comprises contacting ammonium fluoride or ammonium hydrogen difluoride with a compound of formula (II)

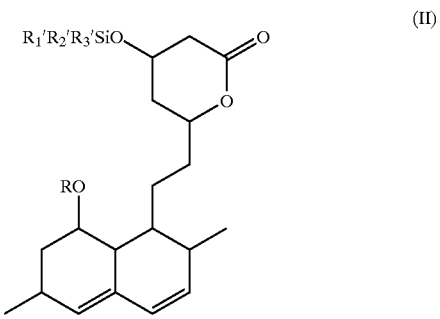

wherein
$R_1'$, $R_2'$ and $R_3'$ may be the same or different and may denote alkyl, aryl or aralkyl; and
R represents:

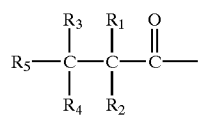

wherein $R_1$, $R_2$, $R_3$, $R_4$ and $R_5$ are as defined above;
in an organic solvent to yield said compound of formula (I).

The above method is carried out as one of the steps in the preparation of simvastatin and derivatives and analogs thereof.

The instant invention is advantageous over the prior art because of negligible corrosion to pilot plant and smaller contents of colored side products generated in the deprotection step. Use of the present invention makes the process of synthesis of simvastatin and derivatives and analogs thereof economically and ecologically acceptable, since used ammonium fluoride or ammonium hydrogen difluoride completely remains in the toluene phase and is not distributed into all solvents such as tetra-n-butylammonium fluoride, thus reducing the problems of solvent regeneration and making the process ecologically more acceptable. Also, the quantities of used solvents are considerably smaller in comparison with the conventional procedures.

The process of deprotection, the subject of the present invention, comprises the contacting of a compound of formula II dissolved in an organic solvent with ammonium fluoride or ammonium hydrogen difluoride.

The organic residues $R_1'$, $R_2'$ and $R_3'$ of the silyloxy protecting group of the compound of formula II may, independently from each other, denote alkyl, aryl or aralkyl. The alkyl group is preferably a lower, straight chain or branched alkyl group, such as methyl, ethyl, n-propyl or iso-propyl and t-butyl; the aryl group is preferably phenyl; and the aralkyl group is preferably triphenylmethyl, benzyl, xylyl and tolyl. Examples for the silyloxy protecting group include t-butyldimethylsilyloxy, trimethylsilyloxy, triethylsilyloxy, isopropyldimethyl-silyloxy, (triphenylmethyl)-dimethylsilyloxy, t-butyldiphenylsilyloxy, methyldiisopropylsilyloxy, tribenzylsilyloxy, tri-p-xylylsilyloxy, triiso-propylsilyloxy or triphenylsilyloxy.

Compounds of formula II may be prepared according to the procedures disclosed in U.S. Pat. No. 4,444,784. The protection reaction is described therein for t-butyldimethylsilyl as the silyloxy protecting group by using a reaction with the corresponding t-butyldimethylchlorosilane, but other protecting groups can be prepared in an analogous manner with the corresponding alkyl, aryl and/or laralkyl substituted chlorosilane.

The reaction of deprotection is carried out at an approprLiate temperature, suitably in the range of 30° to 80° C. and preferably in the range of 40° to 50° C., for an appropriate time, for example for 2 to 8 hours.

The organic solvent is preferably an organic acid or a mixture of an organic acid with another organic solvent. As the organic acid, acetic acid is particularly perferred, but other organic acids can be used as well, such as methanoic acid, trifluoroacetic acid and others, or mixtures thereof with organic solvents such as an acetic acid/ethyl acetate mixture.

The mole ratio of a compound of formula II to ammonium fluoride and ammonium.hydrogen difluoride, respectively, may vary between 1 to 5 and 1 to 15, and preferably between 1 to 8 and to 1 to 12.

The desired reaction product (I) is then isolated and/or purified from the reaction mixture by suitable methods. These methods preferably include extraction steps and crystallization or precipitation steps. In particular, combined double or multiple extraction steps may be carried out, wherein one type of extraction specifically removes non-polar impurities, whereas another type of extraction specifically removes polar impurities. For example, the reaction mixture is first extracted with an alkane solvent such as n-heptane, n-pentane and petrolether, aimed at extracting the non-polar impurities, and the product is then suitably re-extracted, preferably with toluene or a toluene/ethyl acetate mixture. The resulting organic phases are washed with an aqueous medium such as aqueous sodium hydroxide carbonate solution, the organic solvent such as toluene is removed, e.g. by means of evaporation on a rotary evaporator, and the desired substance is then allowed to crystallize from a suitable solvent or solvent mixture. Accordingly, crystallization can be effected, for example, from water/methanol mixtures, alkanes or cycloalkanes or mixtures thereof, such as cyclohexane, a mixture of butylchloride/alkanes (e.g. pentane, hexane, and the like), diisopropylketone/n-heptane, and the like. Particularly efficient removal of impurities from the crude simvastatin and derivatives and analogs thereof after silyl group deprotection was obtained by crystallization from mixtures of alkanes or cycloalkanes, which may be substituted by low alkyl groups, with low alkyl esters of acetic, propionic or butyric acid. Specific examples of alkanes or cycloalkanes include pentane, hexane, heptane, cyclohexane and methylcyclohexane, and specific examples of low alkyl esters include i-propyl, n-propyl and i-buty esters.

If required, the final product can be further purified by employing conventional isolation techniques, such as different types of chromatography (e.g., high performance liquid chromatography, displacement chromatography) or alternate recrystallizations from organic solvents which are water-miscible and poorly miscible or non-miscible in water.

The present invention is illustrated but in no way limited by the following examples.

EXAMPLES

Example 1

Deprotection with Ammoninum Fluoride ($NH_4F$)

78 g of crude t-butyldimethylsilyloxy simvastatin while stirring was dissolved in 220 ml of acetic acid at 45° C. under a nitrogen atmosphere. 40 g of ammonium fluoride was added and stirring was continued under nitrogen atmosphere at 45°–50° C. for additional 4 hours. The progress of the reaction was monitored by HPLC method. When less than 1% of the integrated area of the HPLC chromatogram representing starting t-butyldimethylsilyloxy simvastatin was present in the reaction mixture, after 15 minutes of continued stirrino the mixture was evaporated at a temperature between 50°–60° C. and pressure of 3325 Pa (25 torr) to the volume of 70 ml which was then cooled to room temperature (between 15°–30° C.) and extracted twice with 200 ml of n-heptane. The remainder was re-extracted with 3×200 ml of toluene/ethyl acetate mixture=10:1 (v/v). The toluene fractions were combined and washed with 250 ml of distilled water and then with 2×100 ml of 5% aqueous $NaHCO_3$ solution. In case the pH of the last washing of the waste $NaHCO_3$ phase was not above 8, washing was repeated once more with 100 ml of 5% of aqueous $NaHCO_3$. The toluene phase was then evaporated at 60° C. under reduced pressure, the product was dried at the pressure of an oil pump (under 1 torr). A yield was 48 g of a crude product, which after recrystallization from the methanol/water mixture gave 35 g of simvastatin in the form of crystals.

Example 2

Deprotpection with Ammonium Hydrogen Difluoride ($NH_4$)$HF_2$

The process disclosed in Example 1 was repeated, wherein ammonium hydrogen difluoride was used in place of ammonium fluoride. A crude product (45 g) was allowed to crystallize from cyclohexane giving 31 g of simvastatin.

Example 3

Deprotection with Ammonium Fluoride ($NH_4F$)

134 g of crude t-butyldimethylsilyloxy simvastatin was dissolved while stirring in 450 ml of acetic acid at 45° C. under a nitrogen atmosphere. 80 g of ammonium fluoride was added and stirring was continued under nitrogen atmosphere at 50°–55° C. for additional four hours. The progress of the reaction was monitored by the HPLC method. When less than 5% of the integrated area of the HPLC chromatogram representing starting t-butyldimethylsilyloxy simvastatin was present in the reaction mixture, 100 ml of acetic acid was evaporated at a temperature of 40° C. and a pressure of 3325 Pa (25 torr). The mixture was then cooled to room temperature (between 15 and 30° C.) and extracted with 600 ml of n-heptane. The remainder was re-extracted with 3×400 ml of toluene/ethyl acetate mixture=9:1 (v/v). The toluene fractions were combined and washed with 250 ml of distilled water and then with 3×600 ml of 2% aqueous NaCl solution. The toluene phase was then evaporated at 50° C. at the pressure of an oil pump (under 133 Pa [1 torr]). The yield was 110 g of a crude simvastatin which was then dissolved at 90° C. in 570 ml of methylcyclohexane/i-propyl acetate mixture=7:1 (v/v). As soon as simvastatin was dissolved, the mixture was cooled to a temperature between 30 and 35° C. After two hours the obtained suspension was cooled to 0° C. After 14 hours at 0° C. the crystals were filtered off and washed with 80 ml methylcyclohexane/i-propyl acetate mixture=12:1 (v/v) and then with 80 ml n-pentane. The obtained crystals were dried in vacuum for 4 hours at 30° C. and at the end 74.4 g of simvastatin with a HPLC purity 97% was obtained.

Comparative Example 1
Deprotection with Tetra-n-butylammonium Fluoride 10.35 g of crude 6(R)-[2-(8'(S)-2',2'-dimethylbutyryloxy-2'(S), 6(R)-dimetliyl-1',2',6',7',8',8a-(R) hexahydronaphthyl-1'(S)) ethyl]-4 (R) (dimethyl-terc-butylsilyloxy)-3, 4, 5, 6,-tetrahydro-2H-pyran-2-one (t-butyldimethylsilyloxy simvastatin) was dissolved in 80 ml of tetrahydrofurane (THF). The resulting solution was added to the tetra-n-butylammonium fluoride (32.2 g) solution in the mixture of 5.1 ml of acetic acid and 80 ml of THF. The resulting solution was stirred under a nitrogen atmosphere in the dark at room temperature (20° C.) for 18 hours. The reaction mixture was then diluted with 320 ml of dichloromethane and extracted with 2×480 ml of 2% HCL, 1×480 ml of water and 2×480 ml of saturated NaHCO₃ solution. The dichloromethane phase was dried over Na₂SO₄, filtered and evaporated to-dryness. A yield of a crude resinous product was 7.98 g, which after crystallization from the t-butyl methyl ether/n-hexane mixture=3:1 gave 2.36 g of crystalline simvastatin.

What is claimed is:

1. A process for the preparation of a compound of the following formula (I)

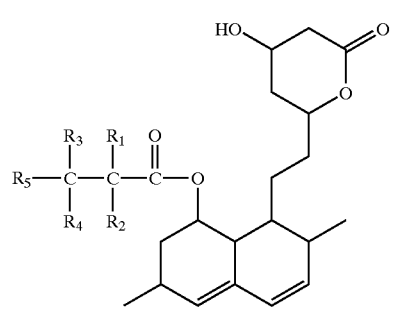

wherein $R_1$, and $R_2$ are independently hydrogen or alkyl with one to ten C atoms;

$R_3$ and $R_4$ are independently hydrogen or alkyl with one to three C atoms;

$R_5$ is hydrogen, halogen or alkyl with one to three C atoms;

characterised in that it comprises contacting of ammonium fluoride or ammonium hydrogen difluoride with a compound of formula (II)

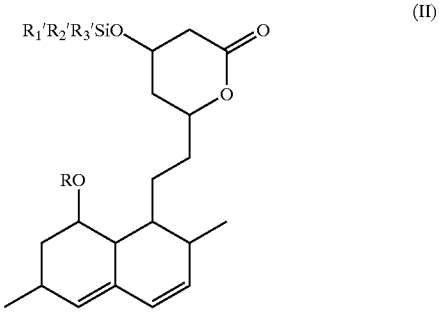

wherein $R_1'$, $R_2'$ and $R_3'$ may be the same or different and may denote alkyl, aryl or aralkyl; and R represents:

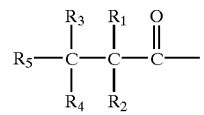

wherein $R_1$, $R_2$, $R_3$, $R_4$ and $R_5$ are as defined above; in an organic solvent to yield said compound of formula (I).

2. The process according to claim 1, wherein the contacting step is carried out at a temperature between 30° and 80° C.

3. The process according to claim 2, wherein the contacting step is carried out at a temperature between 40° and 55° C.

4. The process according to claim 1, wherein the organic solvent is an organic acid or a mixture of an organic acid with another organic solvent.

5. The process according to claim 4, wherein the organic acid is acetic acid.

6. The process according to claim 1, wherein the reaction of deprotection is carried out under an inert atmosphere.

7. The process according to claim 1, wherein, after the contacting step, the reaction mixture is extracted with an alkane solvent.

8. The process according to claim 1 or 7, wherein, after the contacting step and optionally after the alkane solvent extraction step, the reaction mixture is extracted with a mixture of toluene/ethyl acetate.

9. The process according to claim 1 or 7, wherein the yielded compound of formula (I) is purified by means of crystallization from mixtures of alkanes or cycloalkanes, which may be substituted by low alkyl groups, with low alkyl esters of acetic, propionic or butyric acid.

10. The process according to claim 1, wherein the silyloxy protecting group $R_1'R_2'R_3'SiO$—in the compound of formula (II) is selected among the group consisting of t-butyldimethylsilyloxy, trimethylsilyloxy, triethylsilyloxy, isopropyldimethylsilyloxy, (triphenylmiethyl)-dimethylsilyloxy, t-butyldiphenylsilyloxy, methyldiisopropylsilyloxy, tribenzylsilllyloxy, tri-p-xylylsilyloxy, triisopropylsilyloxy, and triphenylsilyloxy.

11. The process according to claim 1, wherein the silyloxy protecting group is t-butyldimethylsilyloxy.

12. A process according to claim 1, wherein the compound obtained is simvastatin.

13. The process according to claim 1, wherein the contacting step is carried out at a temperature between 3° and 80° C.;

the organic solvent comprises acetic acid;

the reaction of deprotonation is carried out under an inert atmosphere;

after the contacting step, the reaction mixture is extracted with alkane solvent and optionally re extracted with a mixture of toluene/ethyl acetate;

the yielded compound of formula (I) is purified by means of crystallization from mixtures of alkanes or cycloalkanes, which may be substituted by low alkyl groups, with low alkyl esters of acetic, proprionic or butyric acid;

the silyloxyl protecting group is t-butyldimethylsilyloxy; and the compound obtained is simvastatin.

* * * * *

UNITED STATES PATENT AND TRADEMARK OFFICE
CERTIFICATE OF CORRECTION

PATENT NO.   : 6,509,479 B1
DATED        : January 21, 2003
INVENTOR(S)  : Marko Zlicar et al.

It is certified that error appears in the above-identified patent and that said Letters Patent is hereby corrected as shown below:

<u>Column 6,</u>
Line 60, replace "triphenylmiethyl" with -- triphenylmethyl --.
Line 62, replace "tribenzylsillyloxy" with -- tribenzylsilyloxy --.

Signed and Sealed this

Thirteenth Day of May, 2003

JAMES E. ROGAN
*Director of the United States Patent and Trademark Office*